(12) United States Patent
Liang et al.

(10) Patent No.: US 8,178,718 B2
(45) Date of Patent: May 15, 2012

(54) CATALYST FOR OXIDATION OF SATURATED AND UNSATURATED ALDEHYDES TO UNSATURATED CARBOXYLIC ACID, METHOD OF MAKING AND METHOD OF USING THEREOF

(75) Inventors: Wugeng Liang, Des Plaines, IL (US); Paul E. Ellis, Sugar Land, TX (US); Joseph R. Linzer, Katy, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 1188 days.

(21) Appl. No.: 11/702,395

(22) Filed: Feb. 5, 2007

(65) Prior Publication Data

US 2008/0188681 A1   Aug. 7, 2008

(51) Int. Cl.
*C07C 51/235* (2006.01)
*B01J 23/887* (2006.01)

(52) U.S. Cl. .................................. 562/535; 502/312
(58) Field of Classification Search .................. None
See application file for complete search history.

(56) References Cited

U.S. PATENT DOCUMENTS

| | | | |
|---|---|---|---|
| 3,761,516 A | | 9/1973 | Khoobiar |
| 3,939,096 A | | 2/1976 | Richardson |
| 3,962,322 A | | 6/1976 | Richardson |
| 3,998,876 A | | 12/1976 | Kato et al. |
| 4,320,227 A | | 3/1982 | Matsumoto et al. |
| 4,347,163 A | * | 8/1982 | Shaw et al. ............... 502/209 |
| 4,358,610 A | * | 11/1982 | Pedersen et al. ........... 562/535 |
| 4,558,029 A | | 12/1985 | Paparizos et al. |
| 4,760,153 A | | 7/1988 | Takahashi et al. |
| 5,087,744 A | * | 2/1992 | Krabetz et al. ............. 562/535 |
| 5,191,116 A | | 3/1993 | Yamamatsu et al. |
| 5,380,932 A | | 1/1995 | Bielmeier et al. |
| 5,935,897 A | * | 8/1999 | Trubenbach et al. ........ 502/172 |
| 6,172,245 B1 | | 1/2001 | Monnier et al. |
| 7,649,111 B2 | | 1/2010 | Liang et al. |
| 2004/0116284 A1 | | 6/2004 | Stevenson et al. |
| 2005/0259658 A1 | | 11/2005 | Logan et al. |
| 2007/0010394 A1 | | 1/2007 | Atsushi et al. |
| 2007/0021296 A1 | | 1/2007 | Liang et al. |
| 2007/0106091 A1 | | 5/2007 | Stevenson et al. |

FOREIGN PATENT DOCUMENTS

| | | |
|---|---|---|
| EP | 0024954 A1 | 3/1981 |
| EP | 0060066 A1 | 9/1982 |
| EP | 1867387 A1 | 12/2007 |

OTHER PUBLICATIONS

Kirk-Othmer, Encyclopedia of Chemical Technology, 4th Edition, 1993, vol. 5, John Wiley &Sons, New York, pp. 383-389.*
International Search Report; International Application No. PCT/US08/01461; International Filing Date Feb. 4, 2008; Date of Mailing May 20, 2008; 2 pages.
Written opinion of the International Searching Authority; International Application No. PCT/US08/01461; International Filing Date Feb. 4, 2008; Date of Mailing May 20, 2008; 6 pages.

* cited by examiner

*Primary Examiner* — Paul A Zucker
(74) *Attorney, Agent, or Firm* — Cantor Colburn LLP

(57) ABSTRACT

The invention is a supported or bound heteropoly acid catalyst composition, a method of making the catalyst composition and a process for the oxidation of saturated and/or unsaturated aldehydes to unsaturated carboxylic acids using the catalyst composition. The catalyst composition has a heteropoly acid component containing molybdenum, vanadium, phosphorus and cesium and support/binder having a surface area of about 0.1 $m^2/g$ to about 1.0 $m^2/g$. The catalyst is made by dissolving compounds of the components of each of the heteropoly acid compounds in a solution, precipitating the heteropoly acid compounds, contacting the heteropoly acid compounds to form a catalyst precursor and calcining the catalyst precursor to form a heteropoly acid compound catalyst. Unsaturated aldehydes, such as methacrolein, may be oxidized in the presence of the heteropoly acid compound catalyst to produce an unsaturated carboxylic acid, such as methacrylic acid.

67 Claims, 2 Drawing Sheets

CATALYST FOR OXIDATION OF SATURATED AND UNSATURATED ALDEHYDES TO UNSATURATED CARBOXYLIC ACID, METHOD OF MAKING AND METHOD OF USING THEREOF

BACKGROUND OF THE INVENTION

1. Field of the Invention

This invention relates to supported or bound heteropoly acid catalyst compositions, a method of making such catalyst compositions and a process for the oxidation of unsaturated aldehydes, such as methacrolein, to unsaturated carboxylic acids, such as methacrylic acid, in a vapor phase reaction using such catalyst compositions.

2. Description of the Prior Art

Various catalysts are known for the gas phase catalytic oxidation of unsaturated aldehydes to unsaturated carboxylic acids. Included are molybdenum-based mixed metal oxides compound which can contain oxides of metals such as phosphorus, arsenic, cesium, rubidium, cobalt, nickel, iron, chromium, antimony, tellurium and silicon in addition to molybdenum. These same metals and others may occur in heteropoly acid compounds as metal oxide clusters forming heteropolyoxoanions in acid form instead of simple metal oxides. Heteropoly acid compounds are also known as catalysts for the gas phase catalytic oxidation of unsaturated aldehydes to unsaturated carboxylic acids. Heteropoly acid compounds have a central metal atom surrounded by a framework of other metal atoms connected to each other and the central metal atom through oxygen atoms. The central metal atom is different ("hetero") from the framework metal atoms.

U.S. Pat. No. 3,998,876 discloses a catalyst of a heteropoly acid compound containing phosphorus, molybdenum, arsenic, at least one of vanadium, tungsten, copper, iron, manganese or tin, at least one of lithium, sodium, potassium, rubidium or cesium and ammonium groups in the form of a salt of the heteropoly acid. The examples of the nonsupported catalyst were shown to have a higher degree of conversion at comparable selectivities compared to a catalyst supported on an alumina/silica carrier.

U.S. Pat. No. 4,320,227 discloses a heteropoly acid catalyst containing molybdenum, vanadium, phosphorus, one or more of copper, tin, thorium, aluminum, germanium, nickel, iron, cobalt, zinc, titanium, lead, rhenium, zirconium, cerium, chromium, bismuth or arsenic, and one or more of potassium, rubidium, cesium or thallium. For improvements in thermal stability and catalyst life and increase in yield of methacrolein and methacrylic acid a suitable carrier, such as silicon carbide, α-alumina, aluminum powder, diatomaceous earth or titanium oxide, can be used. Active carriers which react with heteropoly acids are not preferable.

U.S. Pat. No. 5,191,116 discloses a heteropoly acid catalyst containing molybdenum, vanadium and/or copper, phosphorus and/or arsenic, at least one of an alkali metal, such as lithium, sodium, potassium, rubidium, and cesium, an alkaline earth metal, such as magnesium, calcium, strontium and barium, or thallium and at least one of silver, zinc, cadmium, titanium, zirconium, niobium, tantalum, chromium, tungsten, manganese, iron, cobalt, nickel, boron, aluminum, germanium, rhodium, tin, antimony, bismuth, selenium, tellurium, yttrium, lanthanum, cerium, praseodymium and neodymium. The catalysts may be carried on a carrier, such as silica, α-alumina, titania, zirconia, diatom earth, silica alumina, water soluble silica sol and silicon carbide. Inert carriers having a vast plurality of macropores and high porosity are preferred. One working example used a carrier of silica.

U.S. Pat. Nos. 3,939,096 and 3,962,322 disclose a catalyst for a process for vapor phase conversion of an unsaturated aldehyde, such as acrolein, to the corresponding unsaturated carboxylic, such as acrylic acid. The catalyst is unagglomerarated, supported and of the empirical formula $Mo_aV_bW_cMn_dO_e$ where a is 12, b is 0.5 to 12, c is 0.1 to 6, d is 0.5 to 20 and e is 37 to 94. The support is porous silica particles having a surface area of from about 25 to about 350 $m^2$/gm and a porosity of from about 0.2 to about 1.0 cc/gm. Conversion of methacrolein to methacrylic acid is disclosed as possible with this catalyst.

U.S. Pat. No. 5,380,932 discloses a process for production of methacrylic acid and methacrolein by gas phase oxidation of isobutane with a catalyst of heteropoly acid catalyst compounds of the formula $Cu_aH_bP_cMo_dV_eO_f$ where a=0.1 to 1, b=0 to 7.8, c=0.8 to 1.2, d=9 to 12, e=0.5 to 3 and f depends on the molar numbers a to e, and/or $H_8PMo_{10}VO_{39}$(II) or its anhydride $PMo_{10}VO_{35}$. Carrier material for the catalyst may be large porous carrier particles of zirconia, silicon carbide or silica having a pore volume of from 0.05 to 1.0 $cm^3$/g and a surface area of from 0.01 to 1.0 $m^2$/g. The heteropoly acid catalyst contains molybdenum and vanadium with phosphorus as the central atom, without the presence of any other cationic compounds, and especially without the presence of alkali metal and alkaline earth metal compounds.

U.S. Pat. No. 3,761,516 discloses a metal oxide catalyst for the oxidation of unsaturated aldehydes, such as acrolein and methacrolein, to produce the corresponding unsaturated acids, such as acrylic acid and methacrylic acid. The catalyst is a combination of molybdenum, phosphorus and arsenic with aluminum, copper or cobalt as a promoter on a support or carrier having external macro pores. The pores have a diameter of about 10 microns to about 250 microns and preferably represent 20 to 60 percent of the carrier particle exterior surface. The carrier has a surface area of at most 2 $m^2$/g, preferably 0.01 to 1 $m^2$/g, and most desirably 0.02 to 0.5 $m^2$/g.

SUMMARY OF THE INVENTION

The present invention is for a heteropoly acid catalyst composition, a method of making the catalyst composition and a process of using the catalyst composition for the oxidation of unsaturated aldehydes, such as methacrolein, to unsaturated carboxylic acids, such as methacrylic acid, in a vapor phase reaction. The catalyst composition has a heteropoly acid component and a binder or support. The heteropoly acid component has the general formula $Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences. This catalyst composition is essentially insoluble in water. It is bound with or supported on oxides of magnesium, aluminum, titanium, zirconium, thorium, silicon, boron and mixtures thereof. Embodiments of the invention have the binder or support as an oxide of aluminum (alumina) or of silicon (silica) or as a silica/alumina.

In general, the method of making the catalyst is to dissolve compounds of the catalyst components of the heteropoly acid compound in a solution which may be aqueous and may be acidified, precipitating particles of the catalyst precursor, drying the solid particles and calcining the solid particles.

In general, the process of using the catalyst compositions for the oxidation of unsaturated aldehydes to unsaturated carboxylic acids in a vapor phase reaction is to contact the unsaturated aldehyde, such as methacrolein, with an oxidizing agent, such as air or another oxygen-containing gas, in the presence of the heteropoly acid compound catalyst at conditions to produce an unsaturated carboxylic acid, such as methacrylic acid.

BRIEF DESCRIPTION OF THE DRAWINGS

A more complete appreciation of the invention and many of the attendant advantages thereof will be readily understood by reference to the following detailed description when considered in connection with the accompanying drawings wherein.

DETAILED DESCRIPTION OF THE INVENTION

Figure 1:
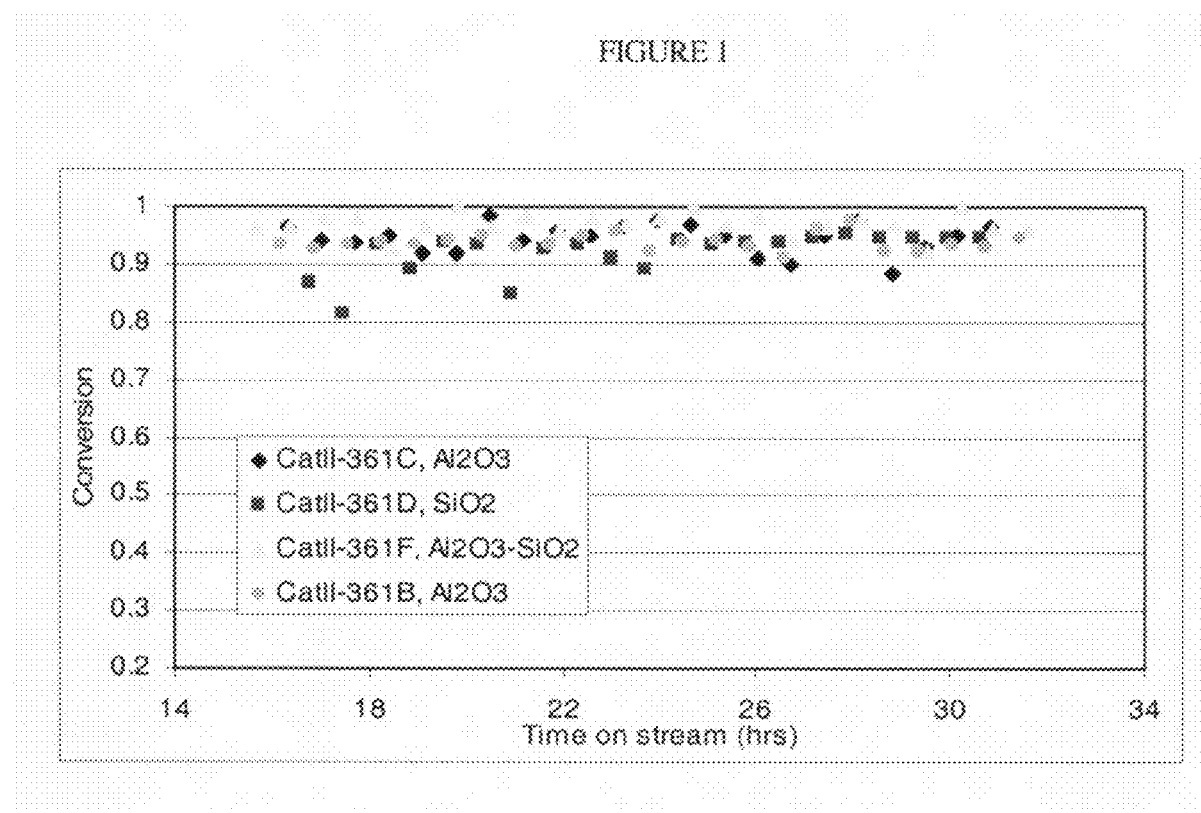
FIG. 1 shows conversion of methacrolein to methacrylic acid over time.

Heteropoly acid compounds containing molybdenum, vanadium and bismuth are effective as catalysts for the oxidation of unsaturated aldehydes, such as methacrolein, to unsaturated carboxylic acids, such as methacrylic acid, in a vapor phase reaction. The catalyst of the present invention has a heteropoly acid component and a support or binder component. The heteropoly acid component has the general formula $Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences.

The heteropoly acid component of the present invention must contain molybdenum, vanadium, phosphorus and cesium. Potassium, rubidium and/or sodium may be present. The heteropoly acid component may contain additional elements, such as copper, bismuth, boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum. One embodiment of the heteropoly acid component has the general formula $Mo_{12}V_aP_bCs_cCu_dM'_eM''_fO_x$ where Mo is molybdenum, V is vanadium, P is phosphorus, Cs is cesium, Cu is copper, M' is bismuth and/or boron, M'' is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a is 0.01 to 5.0, b is 0.5 to 3.5, c is 0.1 to 2.0, d is 0.0 to 1.5, e is 0.0 to 2.0, f is 0.0 to 5.0, and x satisfies the valences.

This catalyst composition is bound with or supported on an inert solid material. "Inert" in this context means a material that is essentially non reactive with the heteropoly acid compound. The binder/support material may be by oxides of magnesium, aluminum, titanium, zirconium, thorium, silicon, boron and mixtures thereof. Specific examples of the binder/support material are an oxide of aluminum (alumina) or of silicon (silica) or is a silica/alumina.

In a method of making the heteropoly acid component compounds containing the elements of the particular heteropoly acid compound are dissolved in a liquid which may be aqueous, aqueous/organic mixtures or organic. In one embodiment of the invention, the liquid is aqueous. The liquid may be acidified to promote dissolution of the compounds. The acid may be organic, such as acetic acid, or inorganic, such as nitric acid. The acidity of the liquid may be completely or partially neutralized by the addition of a base, such as an ammonium-containing compound, e.g. ammonium hydroxide. Precipitation may occur spontaneously as the compounds are mixed together in solution or it may be promoted by heating, cooling or other changes in ambient conditions or by adding a material which will act as a nucleus or "seed" for precipitation of particles. This "seed" material can be a compound containing one or more of the elements of the catalyst composition.

Suitable molybdenum compounds are, but not limited to, ammonium paramolybdate, molybdenum trioxide, molybdenum chloride or mixtures or combinations thereof.

Suitable vanadium components are, but not limited to, ammonium metavanadate, vanadium pentoxide, vanadium chloride or mixtures or combinations thereof.

Suitable phosphorus compounds are, but not limited to, phosphoric acid, ammonium phosphate or mixtures or combinations thereof.

Suitable copper compounds are, but not limited to, copper nitrate, copper chloride or mixtures or combinations thereof.

Suitable bismuth compounds are, but not limited to, bismuth nitrate, bismuth oxide, bismuth chloride or mixtures or combinations thereof.

Suitable boron compounds are, but not limited to, boric acid, boric acid salts, boric oxide, borate esters or mixtures or combinations thereof.

Suitable potassium, rubidium, cesium and sodium compounds are, but not limited to, nitrates, oxides, chlorides or mixtures or combinations thereof.

Suitable antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum compounds are, but not limited to, nitrates, oxides, chlorides or mixtures or combinations thereof.

The heteropoly acid compound and the binder/support material are brought into contact to form a bound or supported catalyst. The weight of the heteropoly acid compound component relative to the weight of the binder/support material component is in the ratio of 1:10 to 10:1, preferably 1:3 to 3:1, more preferably 1:2 to 2:1, most preferably about 1:1.

One purpose of calcination of the catalyst precursor is to activate the catalyst by obtaining an oxide of the metal components. The catalyst precursor may be calcined at a temperature of above about 350° C. for about 2 to about 12 hours. The calcination may be in two stages, one at a temperature lower than about 350° C. for about 1 to about 8 hours and another at a temperature above 350° C. for about 2 to about 12 hours. Calcination may be done in a high temperature oven or kiln.

To obtain a bound or supported heteropoly acid catalyst, the heteropoly acid compound and the binder/support material are mixed together and tableted. The binder/support material may be added during the synthesis prior to precipitation of the heteropoly acid compound, after precipitation of the heteropoly acid compound (before evaporating liquid to leave solid particles), after evaporating liquid to leave solid particles (before drying the solid particles), after drying the solid particles (before calcining the solid particles) or after calcining the solid particles. In one embodiment of the invention, the binder/support material is added after precipitation of the heteropoly acid compound. The present invention includes any synthesis method which produces a heteropoly acid compound which is supported on or bound with the binder/support material.

The binder or support material of the present invention has a surface area of from about 0.001 m$^2$/g to about 25 m$^2$/g. In one embodiment of the invention, the binder or support material has a surface area of from about 0.01 m$^2$/g to about 10 m$^2$/g. In another embodiment of the invention, the binder or support material has a surface area of from about 0.1 m$^2$/g to about 1.0 m$^2$/g.

The process of using the present invention is to contact feedstock containing saturated and/or unsaturated aldehydes with an oxidizing agent in the presence of the heteropoly acid compound catalyst in a vapor phase reaction at reaction conditions to produce an unsaturated carboxylic acid. In one embodiment of the present invention, the feedstock for this process is an unsaturated aldehyde, such as methacrolein, which is the product of an oxidation reaction of an olefin, such as isobutylene, and may contain a recycle of the oxidation of the unsaturated aldehyde, such as methacrolein, to unsaturated carboxylic acids, such as methacrylic acid. Therefore, the feedstock contains, in addition to unsaturated aldehydes, unreacted reactants, inerts and byproducts, such as water, oxygen, nitrogen, carbon monoxide, carbon dioxide, noble gases, acetone, acetic acid, acrolein, methacrylic acid, isobutylene, and other olefins and saturated and unsaturated hydrocarbons. The concentration of unsaturated aldehydes in the feedstock may vary over a wide range. Examples of the concentration of methacrolein are from about 1 vol. % to about 20 vol. % or from about 2 vol. % to about 8 vol. %.

In another embodiment of the present invention, the feedstock contains products and byproducts from a process for hydroformylation of an olefin, such as propylene, to saturated aldehydes, such as butanals, e.g., butanal and isobutanal or isobutyraldehyde. In another embodiment of the present invention, the feedstock contains a combination saturated and unsaturated aldehydes in proportions from about 5 wt % to about 95 wt %. Embodiments of the present invention having saturated aldehydes in the feedstock are described in U.S. patent application Ser. No. 11/198,124 and Ser. No. 11/189,116 which are hereby incorporated by reference.

The oxidizing agent may be air or another oxygen-containing gas. There may be gases or vapors other than oxygen, such as nitrogen, carbon dioxide, noble gases and steam, in the oxidizing agent. The oxidizing agent may be pure oxygen. In one embodiment of the process of the present invention, the amount of oxygen relative to aldehyde would be from 40% less than stoichiometric to 700% more than stoichiometric on a molar basis, preferably 60% more than stoichiometric to 360% more than stoichiometric on a molar basis. In another embodiment of the process of the present invention in which the aldehyde is methacrolein, the amount of oxygen relative to methacrolein is from about 0.3 to about 4, preferably from about 0.8 to about 2.3 by mole ratio.

The process conditions are at a pressure from about 0 atm to about 5 atm, preferably at about 1 atm, and at a temperature from about 230° C. to about 450° C., preferably 250° C. to about 400° C., more preferably about 250° C. to about 350° C.

The reactor for the process of the present invention may be any reactor for a vapor phase reaction*, such as a fixed bed reactor, a fluidized bed reactor or a moving bed reactor.

The invention having been generally described, the following examples are given as particular embodiments of the invention and to demonstrate the practice and advantages thereof. It is understood that the examples are given by way of illustration and are not intended to limit the specification or the claims to follow in any manner.

Catalyst Composition: $Mo_{12}Bi_{0.5}P_{1.5}V_{0.5}Cu_{0.1}Sb_{0.8}Cs_{1.0}B_{0.5}$ 69.7362 g of ammonium paramolybdate and 1.9263 g of ammonium metavanadate were added to 250 mL of deionized water. The mixture is stirred overnight. All particles are dissolved.

0.7671 g of $Cu(NO_3)_2$ was dissolved in 8 mL of deionized water. 6.4169 g of $CsNO_3$ was dissolved in 35 mL of deionized water. 5.6939 g of $H_3PO_4$ (85%) was dissolved in 9 mL of deionized water. 16.991 g of $HNO_3$ (70%) was dissolved in 45 mL of deionized water and 12 mL of $NH_4OH$ and 7.969 g of $Bi(NO_3)_3$ was added to obtain a clear solution. The solutions were added in the following order to the molybdenum-vanadium solution: $CsNO_3$ solution, $H_3PO_4$ solution, $Cu(NO_3)_2$ solutions and $Bi(NO_3)_3$ solution. Yellow particles formed when the $Bi(NO_3)_3$ solution was added. The temperature of the mixture was raised to 95° C.

3.8394 g of $Sb_2O_3$ and 1.0193 g of $H_3BO_3$ were added to the mixture. Water was evaporated from the mixture. The material obtained was dried at 130° C. for 16 hours to obtain solid particles. A part of the material was denitrified at 235° C. for 3 hours. Portions of the solid particles were combined with different binder/support materials. Table 1 shows the different binder/support materials.

TABLE 1

Four binders used with low surface area

| Binder | Surface Area ($m^2/g$) | Pore Volume (cc/g) | Remarks |
|---|---|---|---|
| $Al_2O_3$ | 0.82 | 0.54 | Tri-modal pore |
| $Al_2O_3$ | 0.25 | 0.26 | Mono-modal pore |
| $SiO_2$ | 0.11 | 0.53 | |
| $Al_2O_3$—$SiO_2$ | 0.008 | — | |

Catalysts were made with binder/support materials of Table 1. Portions of the solid particles were mixed with the binder/support material and the mixture was pressed to a cake using a press. Small amounts of water were added to facilitate forming. The formed cake was then crushed and sieved to 20-30 mesh. The sized material was calcined at 370° C. for 5 hours. A catalyst without the binder/support material was also pressed, crushed, sieved and calcined. The catalysts obtained are shown in Table 2.

TABLE 2

Catalysts made with low surface area binders

| Catalyst | Binder used | Binder content (wt %) | Catalyst Surface area ($m^2/g$) | Catalyst Pore volume (cc/g) |
|---|---|---|---|---|
| 1A | — | 0.0% | 9.12 | 0.092 |
| 1B | $Al_2O_3$ (Trimodal pore) | 19.2 | 7.51 | 0.078 |
| 1C | $Al_2O_3$ (Monomodal-pore) | 21.1 | 6.26 | 0.077 |
| 1D | $SiO_2$ | 21.5 | 6.50 | 0.091 |
| 1F | $Al_2O_3$—$SiO_2$ | 24.1 | 6.34 | 0.084 |

For each of the catalysts described herein, 3-6 cc of catalyst were mixed with sufficient quartz chips to make a total volume of 15 cc, which was placed into a downflow reactor having an internal diameter of 0.40 inches. A gas stream consisting of 3.8% methacrolein, 8.0% oxygen, 30% water and the balance as nitrogen was passed over the catalyst bed in the reactor. The volumetric flow rates were varied between 50 and 100 sccm. The internal reactor temperature was varied between 275° C. and 295° C. The reactor pressure was maintained at about 1 atmosphere. The catalyst loading, flow rates and reactor temperature were adjusted such that methacrolein conversions between 70% and 95% were obtained. Reaction products were condensed into a glass trap maintained at 0° C. for a period of one to three hours. The yields of methacrylic acid, acetic acid, and acrylic acid were determined from this liquid. The amount of methacrolein, carbon dioxide, carbon monoxide, and the other byproducts were determined from on-line analysis or the reaction product stream by gas chromatography. The stability of catalysts made with these binders is shown in FIG. 1.

In all of the examples, the catalyst activities reported were adjusted by taking into account differences in methacrolein conversion, reaction temperature and space velocity, due to differences in amount of catalyst or gas flow rate, by assuming that the reaction is net first order in methacrolein concentration and follows an arrhenius-type temperature dependence. Activities of the catalysts are reported in Table 3 relative to the catalyst 1A for which 3.0 cc of catalyst and 50 sccm total flowrate gave 94.1% conversion and 81.7% selectivity at 284° C. The relative activity of catalyst 1A is defined as 1.0. If a catalyst showed an activity 50% higher than catalyst 1A, then this catalyst would have a relative activity of 1.5.

It is well known that selectivity for methacrolein oxidation (and indeed most partial oxidation reactions) is dependent on methacrolein conversion, i.e., as conversion is increased the selectivity to methacrylic acid decreases due to over-oxidation of the methacrylic acid. Given this, the selectivities of two different catalysts must be compared at the same conversion for the comparison to be meaningful. The selectivity of the reference catalyst was measured across a range of conversions, from about 64% to 94% and a curve was fit to the data over this range. The actual selectivities of the Examples were then compared to this reference selectivity curve at the same conversion. The absolute difference between the selectivities of the catalysts of the Examples and the selectivity of the reference curve is reported as "relative selectivity." The relative selectivity of the reference catalyst is defined as 0.0. If the catalyst showed a selectivity 1.0% higher than the reference catalyst or reference curve at the same conversion, then this catalyst would have a relative selectivity of +1.0%.

TABLE 3

Catalytic performance of catalysts made with different binders

| Catalysts | Activity | Selectivity change |
|---|---|---|
| 1A | 1.00 | 0.0 |
| 1B | 0.94 | 0.0 |
| 1C | 0.97 | +3.5% |
| 1D | 0.87 | +3.5% |
| 1F | 0.98 | +3.0% |

Examples of the binder/support material are illustrated above, e.g., tri-modal pore alumina, mono-modal pore alumina, silica and silica-alumina. The data show the bound catalyst's activity is lower than the unbound material based on the same weight amount of catalyst. However, about 20% by weight of the bound/supported catalyst is inert binder/support material. The selectivities of the bound/supported catalysts are the same or better than the unbound/unsupported catalyst. The performance over time of the above four bound/supported catalysts is shown in FIG. 1. It can be seen that there is no significant deactivation. Heteropoly acid compound catalysts bound or supported with low surface area binder/support material show acceptable activity, improved selectivity and stable performance. A bound/supported heteropoly acid compound catalyst would also inherently have better mechanical strength than an unbound/unsupported heteropoly acid compound catalyst.

Figure 2:
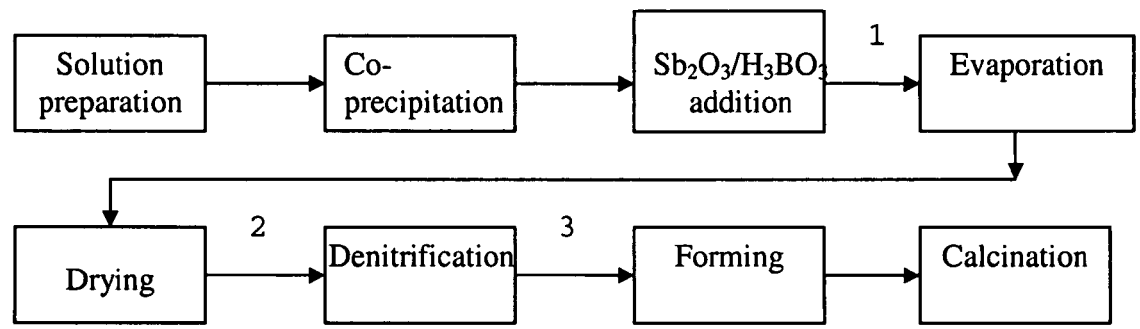
FIG. 2 shows introduction of binder/support at different steps of catalyst preparation.

As shown in FIG. 2, the binder/support material can be introduced at different steps in the synthesis of the heteropoly compound. Binder/support material was added after precipitation and $Sb_2O_3$ and $H_3BO_3$ addition (1), after drying (2), and after denitrification (3). The catalytic performances of these three catalysts prepared by adding binder at different steps of preparation are shown in Table 4.

TABLE 4

Catalytic performance of catalysts made with binder addition at different steps of preparation

| Catalysts | Preparation | Binder content | Activity | Selectivity |
|---|---|---|---|---|
| 1D | Binder added after denitrification | 21.5% | 0.87 | 3.5% |
| 1E | Binder added after drying | 17.9% | 0.65 | 0.0 |
| 3C | Binder added after precipitation and $Sb_2O_3$ and $H_3BO_3$ addition | 16.7% | 0.95 | 5.0% |

It can be seen that relative lower activity is obtained when the binder is added after drying. When the binder is added after drying, most of the time, a lower density catalyst is obtained. The activity in all tables in this report is based on catalyst volume. If the activity is calculated based on the weight of catalyst loaded, the weight based activity of 1E will be close to that of 1D. Better selectivity is obtained when the binder is added just after precipitation and $Sb_2O_3$ and $H_3BO_3$ addition. No selectivity improvement is observed with 1E.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process of preparing a supported or bound heteropoly acid compound comprising:
    a) preparing a heteropoly acid compound of the general formula:

$Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences; and
    b) bringing the heteropoly acid compound into contact with a support or binder having a surface area of less than 1.0 m²/g and pore volume greater than 0.2 cc/g to form a supported or bound heteropoly acid catalyst precursor.

2. The process of claim 1 wherein the heteropoly acid compound is prepared, by:
    a) mixing a solution of a molybdenum compound, a vanadium compound, a phosphorus compound and a cesium compound;
    b) precipitating solid particles
    c) evaporating liquid to leave solid particles;
    d) drying the solid particles; and
    e) calcining the solid particles.

3. The process of claim 2 wherein the support or binder is brought into contact with the heteropoly acid compound after step b), c), d) or e).

4. The process of claim 3 wherein the support or binder is brought into contact with the heteropoly acid compound after step c).

5. The process of claim 2 wherein the molybdenum compound is ammonium paramolybdate, molybdenum trioxide, molybdenum chloride or mixtures or combinations thereof.

6. The process of claim 2 wherein the vanadium compound is ammonium metavanadate, vanadium pentoxide, vanadium chloride or mixtures or combinations thereof.

7. The process of claim 2 wherein the phosphorus compound is phosphoric acid, ammonium phosphite or mixtures or combinations thereof.

8. The process of claim 2 wherein the potassium, rubidium, cesium and sodium compounds are nitrates, oxides, chlorides or mixtures or combinations thereof.

9. The process of claim 2 wherein the solution is aqueous, aqueous/organic mixtures or organic.

10. The process of claim 9 wherein the solutions are aqueous.

11. The process of claim 2 wherein the solution is acidified to promote dissolution of the compounds.

12. The process of claim 11 wherein the acid is organic or inorganic.

13. The process of claim 12 wherein the acid is acetic acid.

14. The process of claim 12 wherein the acid is nitric acid.

15. The process of claim 11 wherein the acidified solution is completely or partially neutralized by the addition of a base.

16. The process of claim 15 wherein the base is an ammonium-containing compound.

17. The process of claim 16 wherein the base is ammonium hydroxide.

18. The process of claim 1 wherein the weight of the heteropoly acid compound component relative to the weight of the support or binder is in the ratio of 1:10 to 10:1.

19. The process of claim 18 wherein the ratio is 1:3 to 3:1.

20. The process of claim 19 wherein the ratio is 1:2 to 2:1.

21. The process of claim 20 wherein the ratio is about 1:1.

22. The process of claim 2 wherein the heteropoly acid catalyst precursor is calcined at a temperature of above about 350° C. for about 2 to about 12 hours.

23. The process of claim 2 wherein the calcination is in two stages, one at a temperature lower than about 350° C. for about 1 to about 8 hours and another at a temperature above 350° C. for about 2 to about 12 hours.

24. The process of claim 1 wherein the heteropoly acid compound is of the general formula:

$$Mo_{12}V_aP_bCs_cCu_dM'_eM''_fO_x$$

where Mo is molybdenum, V is vanadium, P is phosphorus, Cs is cesium, Cu is copper, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a is 0.01 to 5.0, b is 0.5 to 3.5, c is 0.1 to 2.0, d is 0.0 to 1.5, e is 0.0 to 2.0, f is 0.0 to 5.0, and x satisfies the valences.

25. The process of claim 24 wherein the heteropoly acid compound is prepared by mixing a solution of a molybdenum compound, a vanadium compound, a phosphorus compound, a cesium compound, a copper compound, one or more M' compound and one or more M" compound.

26. The process of claim 25 wherein the potassium, rubidium, cesium and sodium compounds are nitrates, oxides, chlorides or mixtures or combinations thereof.

27. The process of claim 25 wherein the copper compound is copper nitrate, copper chloride or mixtures or combinations thereof.

28. The process of claim 25 wherein the bismuth compound is bismuth nitrate, bismuth oxide, bismuth chloride or mixtures or combinations thereof.

29. The process of claim 25 wherein the boron compound is boric acid, boric acid salts, boric oxide, borate esters or mixtures or combinations thereof.

30. The process of claim 25 wherein the antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum compounds are nitrates, oxides, chlorides or mixtures or combinations thereof.

31. The process of claim 1 wherein the supported or bound heteropoly acid catalyst is water insoluble.

32. The process of claim 1 wherein the support or binder is alumina, silica or silica-alumina.

33. The process of claim 1 wherein the support or binder is tri-modal pore alumina, mono-modal pore alumina, silica or silica-alumina.

34. The process of claim 1 wherein the support or binder is mono-modal pore alumina, silica or silica-alumina.

35. A supported or bound heteropoly acid compound catalyst comprising:
a) a heteropoly acid compound of the general formula:

$$Mo_{12}V_aP_bCs_cO_x$$

where Mo is molybdenum, V is vanadium, P is phosphorus, Cs is cesium, O is oxygen, a is 0.01 to 5.0, b is 0.5 to 3.5, c is 0.01 to 2.0 and x satisfies the valences; and b) a support or binder for the heteropoly acid compound having a surface area of less than 1.0 m²/g and pore volume greater than 0.2 cc/g.

36. A supported or bound heteropoly acid compound catalyst, wherein the heteropoly acid compound of the catalyst is of the general formula:

$$Mo_{12}V_aP_bCs_cCu_dM'_eM''_fO_x$$

where Mo is molybdenum, V is vanadium, P is phosphorus, Cs is cesium, Cu is copper, M' is bismuth and/or boron, M" is one or more of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum, O is oxygen, a is 0.01 to 5.0, b is 0.5 to 3.5, c is 0.1 to 2.0, d is 0.0 to 1.5, e is 0.0 to 2.0, f is 0.0 to 5.0, and x satisfies the valences; and a support or binder for the heteropoly acid compound, the support having a surface area of less than 1.0 m²/g and pore volume greater than 0.2 cc/g.

37. The catalyst of claim 35 wherein the weight of the heteropoly acid compound component relative to the weight of the binder/support material is in the ratio of 1:10 to 10:1.

38. The catalyst of claim 37 wherein the ratio is 1:3 to 3:1.

39. The catalyst of claim 38 wherein the ratio is 1:2 to 2:1.

40. The catalyst of 35 wherein the supported or bound heteropoly acid compound catalyst is water insoluble.

41. The catalyst of claim 35 wherein the support or binder is alumina, silica or silica-alumina.

42. The catalyst of claim 41 wherein the support or binder is tri-modal pore alumina, mono-modal pore alumina, silica or silica-alumina.

43. The catalyst of claim 42 wherein the support or binder is mono-modal pore alumina, silica or silica-alumina.

44. A process for converting saturated and/or unsaturated aldehydes to unsaturated carboxylic acids comprising contacting a saturated and/or unsaturated aldehyde with an oxidizing agent in the presence of a supported or bound heteropoly acid catalyst comprising:
a) a heteropoly acid compound of the general formula:

$Mo_{12}V_aP_bCs_cO_x$ where Mo is molybdenum, V is vanadium, P is phosphorus, Cs is cesium, O is oxygen, a is 0.01 to 5.0, b is 0.5 to 3.5, c is 0.01 to 2.0 and x satisfies the valences;

b) a support or binder for the heteropoly acid compound having a surface area of less than 1.0 m²/g and pore volume greater than 0.2 cc/g.

45. The process of claim 44 wherein the concentration of unsaturated aldehydes is from about 1 vol. % to about 20 vol. % of methacrolein.

46. The process of claim 45 wherein the concentration of unsaturated, aldehydes is from about 2 vol. % to about 8 vol. %, of methacrolein.

47. The process of claim 45 wherein the oxidizing agent is air or another oxygen-containing gas.

48. The process of claim 47 wherein the oxidizing agent contains nitrogen, carbon dioxide, noble gases and steam in addition to oxygen.

49. The process of claim 47 wherein the oxidizing agent is oxygen.

50. The process of claim 49 wherein the amount of oxygen relative to aldehyde is from 40% less than stoichiometric to 700% more than stoichiometric on a molar basis.

51. The process of claim 50 wherein the amount of oxygen relative to aldehyde is 60% more than stoichiometric to 360% more than stoichiometric on a molar basis.

52. The process of claim 45 wherein the aldehyde is methacrolein and the amount of oxygen relative to methacrolein is from about 0.3 to about 4 by mole ratio.

53. The process of claim 52 wherein the amount of oxygen relative to methacrolein is from about 0.8 to about 2.3.

54. The process of claim 45 wherein pressure is from about 0 atm to about 5 atm.

55. The process of claim 54 wherein the pressure is about 1 atm.

56. The process of claim 45 wherein temperature is from about 230° C. to about 450° C.

57. The process of claim 56 wherein the temperature is from about 250° C. to about 400° C.

58. The process of claim 57 wherein the temperature is from about 250° C. to about 350° C.

59. The process of claim 45 wherein the supported or bound heteropoly acid compound catalyst is water insoluble.

60. The process of claim 45 wherein a saturated aldehyde is contacted with an oxidizing agent in the presence of a supported or bound heteropoly acid catalyst.

61. The process of claim 60 wherein the saturated aldehyde is isobutanal or isobutyraldehyde.

62. The process of claim 45 wherein a saturated aldehyde and an unsaturated aldehyde is contacted with an oxidizing agent in the presence of a supported or bound heteropoly acid catalyst.

63. The process of claim 62 wherein the saturated aldehyde and the unsaturated aldehyde is in proportions from about 5 wt % to about 95 wt %.

64. The process of claim 45 wherein the support or binder is alumina, silica or silica-alumina.

65. The process of claim 64 wherein the support or binder is tri-modal pore alumina, mono-modal pore alumina, silica or silica-alumina.

66. The process of claim 65 wherein the support or binder is mono-modal pore alumina, silica or silica-alumina.

67. The catalyst of claim 35 wherein the heteropoly acid compound is of the formula $Mo_{12}Bi_{0.5}P_{1.5}V_{0.5}Cu_{0.1}Sb_{0.8}Cs_{1.0}B_{0.5}$.

* * * * *